«12» United States Patent [19]
Tsubaki et al.

[11] Patent Number: 5,472,686
[45] Date of Patent: Dec. 5, 1995

[54] COSMETIC FORMULATIONS

[75] Inventors: Suguru Tsubaki; Isao Noda, both of Kanagawa, Japan

[73] Assignee: Nippon Unicar Company Limited, Ohtemachi, Japan

[21] Appl. No.: 812,570

[22] Filed: Dec. 20, 1991

[51] Int. Cl.$^6$ .................. A61K 7/42; A61K 7/44
[52] U.S. Cl. .................. 424/59; 424/60; 514/844
[58] Field of Search .................. 424/60, 59, 68; 514/844

[56] References Cited

U.S. PATENT DOCUMENTS

| 4,136,239 | 1/1979 | Rossmy | 521/111 |
| 4,150,048 | 4/1979 | Schilling, Jr. et al. | 260/448.2 |
| 4,421,769 | 12/1983 | Dixon et al. | 424/358 |
| 5,100,658 | 3/1992 | Bolich, Jr. et al. | 424/70 |

FOREIGN PATENT DOCUMENTS

| 0150603 | 12/1984 | European Pat. Off. | 260/448.2 |
| 0331833 | 5/1988 | European Pat. Off. | 424/59 |
| 0374332 | 12/1988 | European Pat. Off. | 424/59 |
| 0492657 | 12/1991 | European Pat. Off. | 424/70 |
| 1103201 | 2/1968 | United Kingdom . | |

OTHER PUBLICATIONS

Japanese Abstract, vol. 13, No. 427 dated Sep. 22, 1989.

Primary Examiner—Dale R. Ore
Attorney, Agent, or Firm—Andrew S. Reiskind

[57] ABSTRACT

Conventionally, polyether pendant dimethyl polysiloxane and linear polyether-polysiloxane-polyether block copolymer have been frequently proposed and dominantly used in cosmetic formulations. In this invention, non-hydrolyzing block copolymers comprising a linear polysiloxane-polyoxyalkylene block as a repeating unit are used as a main component of cosmetic formulations used in skin care products and hair care products.

10 Claims, No Drawings

COSMETIC FORMULATIONS

FIELD OF THE INVENTION

This invention relates to cosmetic formulations comprising a specific polysiloxane-polyoxyalkylene copolymer.

More specifically, this invention relates to cosmetic formulations useful in skin care and hair care products which are characterized by comprising a non-hydrolyzing block copolymer having as a repeating unit a linear polysiloxane-polyoxyalkylene block.

BACKGROUND OF THE INVENTION

There are many kinds of skin care products for different purposes, such as cleansing cream, cold cream, hand cream, powder, lotion, foundation, mascara, eye shadow, lipstick, manicure, anti-sunburn cream, etc. It is necessary that they have clean impression, good touch, good application, no makeup destruction, durability and retention, but easy removability from the skin when washed by face washing cosmetics, water or the like. Some of these properties are incompatible with each other. Skin care products having most or all of these properties are desired.

As main components of these skin care products, liquid paraffin, paraffin wax, aliphatic acid, higher alcohol, animal fats and oils, and vegetable oils, synthetic esters, polyalkyleneglycol derivatives, silicone compounds, etc. are used. Silicone compounds have been noted because of their special properties, e.g., durability, water resistance, affinity with the skin, moisture retention, gloss imparting property, water repellency, flexibility, vapor permeability, gas permeability, film forming property, filler retaining property, lubricancy, etc., and applications of various silicon compounds to skin care products have been proposed. What has been proposed, for example, includes dialkylpolysiloxane (Japanese Patent Laid-Open Publication No. 119036/1979), amino group-content polysiloxane (Japanese Patent Laid-Open Publication No. 58605/1982), pendant polysiloxane-polyoxyalkylene copolymer (Japanese Patent Laid-Open Publication No. 131910/1983, Japanese Patent Laid-Open Publication No. 197432/1984), silicone resin (Japanese Patent Laid-Open Publication No. 298518/1987), esterified polysiloxane (Japanese Patent Laid-Open Publication No. 150288/1988), dimethyl cyclopolysiloxane (Japanese Patent Laid-Open Publication No. 159489/1988), etc.

Polysiloxanes having no hydrophilic groups are difficult to solvate in water-based solvents, and large amounts of emulsifying agents are needed which can impair the transparency of the emulsified liquids, irritate the skin, and lower water resistance. Unpreferably, amino group content polysiloxane yellows. A number of polyoxyalkylene group pendant dialkylpolysiloxanes have been proposed, but they have insufficient water resistance, retention, skin touch, gloss, etc. Silicone resin requires the use of low molecular weight cyclosiloxanes and isopentane, or other solvents, and its use is limited. Esterified polysiloxanes can have improved properties, but are considerably higher in cost.

Accordingly, skin care products comprising cosmetic formulations which can reduce the disadvantages of the conventional silicone compounds as described above, but retain the desired properties of water resistance, durability, retention, skin touch and gloss are desired.

Hair is washed by shampoo, treated with rinse, protected by hair dressing, mousse and set by hair spray. In some cases, permanent liquid and hair dye are used. Compositions used for hair treatment contain cosmetic formulations and are often blended with vegetable oil, animal oil, mineral oil, synthetic oil, etc. to form hair care products.

With the recent progress of silicone polymer technology, various polysiloxane polymers have been blended as main components of cosmetic formulations used in hair care products because of their desirable characteristics.

Such hair care products are exemplified by: shampoos containing dimethyl silicone, diethyl silicone, methylphenyl or silicone, to give rinse effect (U.S. Pat. No. 2,826,551); a hair cosmetic containing a diol derivative or branched aliphatic alcohol and methyl polysiloxane (Japanese Patent Laid-Open Publication No. 47923/1977); a conditioning lotion containing vinyl pyrrolidone-silicone copolymer (Japanese Patent Laid-Open Publication No. 57337/1977); a cosmetic containing quarternary nitrogen-content cationic modified silicone (Japanese Patent Laid-Open Publication No. 66506/1980); a hair treatment composition comprising an anionic polymer compound, a cationic surfactant and oxyalkylene modified organopolysiloxane (Japanese Patent Laid-Open Publication No. 108811/1980); a hair conditioner composition comprising polyoxyalkylene modified organopolysiloxane and water-containing ethanol or absolute ethanol (Japanese Patent Laid-Open Publication No. 136214/1980); a hair cosmetic comprising water, ethanol, a phosphoric ester salt of polyoxypropylene multivalent-alcohol ether and polyoxyalkylene methylpolysiloxane (Japanese Patent Laid-Open Publication No. 16405/1981); a hair cosmetics containing organosiloxanepolyoxyalkylene copolymer (Japanese Patent Laid-Open Publication No. 22712/1981); a hair conditioner composition comprising polysiloxane containing aminoalkyl groups and hydroxy groups, a cationic polymer and an aqueous carrier (Japanese Patent Laid-Open Publication No. 45406/1981); a shampoo composition comprising an anionic surface active agent, a cationic polymer and a silicone derivative (dimethyl polysiloxane, methylphenyl polysiloxane, polyether modified silicone oil, epoxy modified silicone oil, fluorine modified silicone oil, alcohol-modified silicone oil and alkyl-modified silicone oil) (Japanese Patent Laid-Open Publication No. 72095/1981); a hair cosmetic comprising an olefin liquid polymer, dimethyl polysiloxane, a polymeric chain emulsifying agent and water (Japanese Patent Laid-Open Publication No. 86113/1981); a hair cosmetic comprising quarternary ammonium salt, higher alcohol, and hydrophobic silicone (Japanese Patent Laid-Open Publication No. 92808/1981); an amphoteric acrylic resin, polyoxyalkylene modified organopolysiloxane, and polyethylene glycol (Japanese Patent Laid-Open Publication No. 92811/1981); a hair conditioner comprising as the main component organopolysiloxane having at least one aminoalkyl group, and at least one oxyalkylene group, polyoxyalkylene or hydroxyalkyl group (Japanese Patent Laid-Open Publication No. 74602/1983); a cosmetic containing an amphoteric silicone oil and polyoxyalkylene-modified polysiloxane (Japanese Patent Laid-Open Publication No. 126209/1985); a hair conditioning composition comprising a silicone conditioner, dimethyl silicone copolymer, a lipid vehicle formulation, a cationic surface active agent vehicle formulation and water (Japanese Patent Laid-Open Publication No. 6/1986); a hair coloring composition comprising a coloring agent component, silicone oil and water (Japanese Patent Laid-Open Publication No. 83111/1986); and a hair cosmetic comprising an organosilicon resin and volatile hydrocarbon oil (Japanese Patent Laid-Open Publication No. 158914/1986).

Hair care products which contain dimethyl polysiloxane as one component often have problems in that the dimethyl polysiloxane does not solvate in aqueous solvents, and therefore, large amounts of emulsifying agents are needed which can impair transparency of the emulsified liquids, irritate the skin, and degrade their water resistance after being applied to the hair. In addition, dimethyl polysiloxane tends to generate static which tends to attract dust and grime and cause the hair fly phenomenon.

The polysiloxanes having aminoalkyl group and/or quarternary nitrogen-containing groups are considerably improved in antistatic effect, water resistance and durability, but do not have all these properties. A number of hair care products containing dimethyl polysiloxane having polyoxyalkylene groups have been proposed, and they have succeeded in preventing the generation of static, but their water resistance, combability, bulky finish, emulsification, foaming are not sufficient.

Accordingly, hair care products comprising cosmetic formulations which reduce the disadvantages of the conventional dimethyl polysiloxane or various functional groups containing polysiloxanes and retain the desired hair antistatic effect, moisture retaining effect, combing, brilliant finish, voluminous finish, bulky finish, wetty finish, emulsification effect and foaming effect are desired.

SUMMARY OF THE INVENTION

By this invention cosmetic formulations comprising a non-hydrolyzing block copolymer having a linear polysiloxane-polyoxyalkylene block as a repeating unit are provided which are suitable for use in skin care products and hair care products.

Preferably, the block copolymer used in this invention is expressed by the general formula:

$$([Y(R_2SiO)_aR_2SiYO] [(C_nH_{2n}O)_b])_c$$

wherein; R represents a monovalent hydrocarbon radical containing substantially no unsaturated aliphatic series; n is an integer of 2–4; b is an integer of at least 4; c is an integer of at least 4; a is an integer of at least 5; Y represents a divalent organic group which is bonded with an adjacent silicon atom by a carbon-silicon linkage and with a polyoxyakylene block by an oxygen atom; the average molecular weight of each siloxane block is about 400–about 10,000; the average molecular weight of each polyoxyakylene blocks is about 300 – about 10,000; the siloxane blocks are about 10 –about 90 weight % of the block copolymer; and the block copolymer has an average molecular weight of at least about 3,000.

The cosmetic formulations of the present invention, when used in skin care products, can provide advantages in at least one of the following properties; smooth touch when applied to the skin, non-tackiness, wetness, brilliance, durability on the skin and retention of the beneficial effect the other components.

The cosmetic formulations of the present invention, when used in hair care products can provide advantages in at least one of the following properties; combing, smoothness, wetness, flexibility, brilliance, bulkiness, coating effect, durability, tackiness, texture, emulsification effect, hair fly, dust attraction and moisture retention.

DETAILED DESCRIPTION OF THE INVENTION

The above-described cosmetic formulation is produced by reacting a compound A having the general formula:

$$HR_2SiO(R_2SiO)_aSiR_2H$$

with a compound B having the general formula:

$$CH_2=\overset{R'}{\underset{|}{C}}CH_2O(C_nH_{2n}O)_bCH_2\overset{R'}{\underset{|}{C}}=CH_2$$

wherein R represents a monovalent hydrocarbon radical, R' represents a monovalent hydrocarbon which may be the same or different from R, n is an integer of 2 to 4, a is an integer of at least 4, and b is an integer of at least 4.

The R and R' in the above-described formulas are selected from the group consisting of alkyl, e.g., methyl, ethyl, propyl, isopropyl, butyl, pentyl, hexyl, octyl, decyl, dodecyl, octadecyl, eicosyl, etc., aryl group, e.g., phenyl, naphthyl, etc., aralkyl, e.g. , benzyl, phenylethyl, etc., tolyl, xylyl, and cyclohexyl, and can be the same or different.

The divalent organic group represented by Y in the above-described formula is exemplified by:

$$-R''-, -R''-CO-, -R''-NHCO-, -R''-NHCONH-$$
$$R'''-NHCO-, -R''-OCONH- R'''-NHCO$$

where R" is a divalent alkylene group, e.g., ethylene, propylene, butylene, and R''' is a divalent alkylene group, e.g., R" or a divalent arylene group exemplified by:

$$-C_6H_4-, -C_6H_4-, -C_6H_4-CH_2-C_6H_4-,$$
$$-C_6H_4-CH(CH_3)_2-C_6H_4-$$

and preferably R''' is a phenylene group.

More preferable examples of the divalent organic group are:

$$-CH_2CH_2-, -CH_2CH_2CH_2-, -CH_2CH_2CH_2CH_2-,$$
$$-(CH_2)_2CO-, -(CH_2)_3NHCO-,$$
$$-(CH_2)_3NHCONHC_6H_4NHCO-, \text{ and}$$
$$-(CH_2)_3OCONHC_6H_4NHCO-.$$

Most preferably, Y is a divalent alkylene group, specifically $-CH_2CH_2CH_2-$.

The non-hydrolyzing copolymer can be produced by reacting a polyoxyalkylene compound having reactive end groups with dihydrocarbyl siloxane liquid having end groups which are reactive with the end groups of the polyoxyalkylene compound.

The nature of these reactive end groups determine the structure of the divalent organic group represented by Y. Generally the nature of the end groups of a reaction product depends on the end groups of reactive substances. Such reactions are expressed by the following reaction formulas:

$$wCH_2=CHCH_2O(C_nH_{2n}O)_bCH_2CH=CH + wHSiMe_2O(SiMe_2)_aSiMe_2H \longrightarrow \quad (a)$$

$$[(CH_2)_3O(C_nH_{2n}O)_b(CH_2)_3SiMe_2O(SiMe_2O)_aSiMe_2]_c$$

-continued

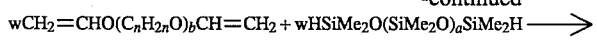 (b)

 (c)

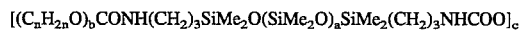

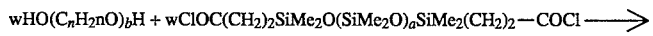 (d)

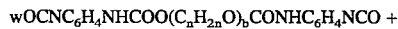 (e)

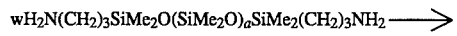

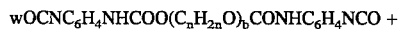 (f)

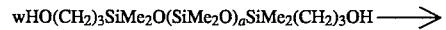

In these formulas, the polyoxyalkylene block includes polyoxyethylene, polyoxypropylene, polyoxybutylene, mixed polyoxyethylene/oxypropylene, etc.

The most preferable example is the block copolymer which is produced by reacting a polyoxyalkylene compound having $CH_2=C(CH_3)-CH_2-$ groups on both ends with dimethylpolysiloxane having $HSi(CH_3)_2O$-groups on both ends, and expressed by the formula;

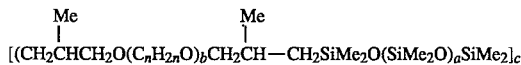

where; Me represents a methyl group; n is an integer of 2–4; a is an integer of at least 4; b is an integer of at least 4; and c is an integer of at least 4.

The block copolymer used in the cosmetic formulations of this invention is used singly or solvated in various organic solvents, e.g., ethanol, isopropyl alcohol, ethylene glycol, propylene glycol, pentane, hexane, octane, nonane, decane, etc.

Hair and skin care products can be prepared by blending the cosmetic formulations of this invention with known personal care ingredients, such as:

- an oil which is used as a component of the usual hair cosmetics, e.g., camellia oil, rapeseed oil, sesame oil, safflower oil, cottonseed oil, castor oil, soybean oil, coconut oil, palm oil, beewax, montanic wax, lanolin, squalane or silicone oil;
- a surface active agent, e.g., alkyl benzenesulfonate, polyoxyalkylene alkylsulfate ester, alkylsulfate ester, alkanesulfonate, alkyl ethoxycarboxylate, succinic derivatives, alkylamine oxide, imidazoline compounds, polyoxyethylene alkyl or alkenyl ether, polyoxyethylene alkyl phenyl ether, higher fatty acid alkanolamide or its alkylene oxide addition products;
- high-molecular compounds, e.g., cellulosic compounds, such as, hydroxyethyl cellulose, hydroxypropyl cellulose, hydroxypropyl methyl cellulose, methyl cellulose, cationic cellulose, cationic polymers, polyvinylpyrrolidone, vinylpyrrolidone-vinyl acetate copolymer, vinylpyrrolidone-vinyl acetate-alkyl a aminoacrylate copolymer, lower alkyl half ester of methyl vinyl ether-maleic anhydride copolymer, vinyl acetatecrotonic acid copolymer, acrylic acid-acrylic ester-N-alkyl acrylamide copolymer;
- a moisture retaining agent, e.g., glycerol, ethylene glycols, propylene glycols, sorbitol, maltitol, pyrrolidone sodium carboxylate, polyoxyethylene methylglycoside, polyoxypropylene methylglycoside, glycol;
- an amino acid, e.g., glycine, serine, proline;
- a powder, e.g., (sericite, silica-alumina, silica gel, kaolin, talc, red iron oxide, ultramarine, mica, mica titanium, magnesium oxide, chromium oxide, antimony oxide, zinc monoxide, zinc dioxide, magnesium carbonate, calcium carbonate, calcium phosphate, barium sulfate, aluminum hydroxide, chromium hydroxide, magnesium metasilicate aluminate, magnesium silicate aluminate, polyethylene powder); and
- antioxidants, UV absorbers, perfumes, dyes, pigments, coloring matters, preservatives, vitamins, hormones, deodorants, binders, extinguishing agents etc.

In the case the cosmetic formulations of this invention are used in aerosol-type sprays, a pressurizing agent, e.g., propane, butane, trichloromonofluoromethane, dichloro-difluoromethane, dichlorotetrafluoroethane, carbon dioxide or nitrogen gas, may additionally be present in the formulation.

Typical examples of the use of the cosmetic formulations of this invention in the hair care products formulations include shampoo, rinse, hair lotion, hair oil, hair cream, pomade, hair spray, setting lotion, permanent wave liquid, mousse, dye, shaving foam, etc. The hair cosmetic formulations are suitable for use on the hair, beard, underarm hair, chest hair, artificial hair, as of wigs, etc., hair and features of pets, e.g., dogs, cats, monkeys, macaws, canaries, etc. When the cosmetic formulations are used in hair care products, these resultant cosmetics are superior to the conventional hair cosmetics in combing, smoothness, wetness, flexibility, brilliance, voluminousness (bulkiness), coating effect, durability, tackiness, texture, emulsification effect, hair fly, dust attraction, moisture retention, etc.

Typical examples of the use of these cosmetic formulations of this invention in skin care products include cleansing cream, cold cream, hand cream, powder, lotion, foundation, mascara, eye shadow, lipstick, manicure, anti-sunburn creams etc. When these cosmetic formulations are used in skin care products, the resultant cosmetics are superior to the conventional ones in smooth touch when applied to the skin, non-tackiness, wetness, brilliance, durability on the skin, retention of the beneficial effects of the other components, etc.

EXAMPLES

The following examples are provided for illustrative purposes and are not intended to limit the scope of the claims that follow.

Example 1: Synthesis

One hundred (100) g of dimethacrylpolyether ($CH_2=C(CH_3)CH_2O(C_2H_4O)_{18}$ $(C_3H_6O)_{33}$ $CH_2C(CH_3)=CH_2$), 350 g of toluene, and 20 ppm of platinum as chloroplatinate were put in a 500 ml-three neck flask having a mechanical agitator, a condenser, a thermometer and a port for feeding nitrogen. One hundred nine (109) g of dihydropolydimethyl polysiloxane ($HMe_2SiO(MeSiO)_{40} SiMe_2H$) was gradually added to the mixture at such a speed that the temperature is retained at 80°–100 °C.

The end of this reaction was judged when an $AgNO_3$ test on SiH became minus.

Then the reacted mixture was neutralized by $NaHCO_3$ and filtered, and the solvent was removed at 50° C./1 mmHg by a rotary evaporator. Two hundred and three (203) g of the block copolymer having the following repeating unit and a molecular weight of 95,000 was prepared.

$$[(Me_2SiO)_{41}Me_2SiCH_2CH(CH_3)CH_2—O(C_2H_4O)_{18}—(C_3H_6O)_{33}CH_2CH(CH_3)CH_2]_{16.1}$$

Example 2; Synthesis

Using the same conditions as in Example 1, 70 g of dimethacryl polyether $CH_2=C(CH_3)CH_2O(C_2H_4O)_{20}(C_3H_6O)_{29}CH_2C(CH_3)=CH_2$, 61 g of dihydropolydimethylsiloxane $HMe_2SiO(MeSiO)_{30}SiMe_2H$, 350 g of toluene, and 20 ppm of platinum as an addition catalyst were reacted. One hundred and twenty-six (126) g, of the block copolymer having a molecular weight of 67,000 and having the following repeating unit was prepared.

$$[(Me_2SiO)_{31}Me_2SiCH_2CH(CH_3)CH_2—O(C_2H_4O)_{20}—(C_3H_6O)_{29}CH_2CH(CH_3)CH_2]_{13.3}$$

Example 3: Synthesis

Using the same conditions as in Example 1, 150 g of dimethacryl polyether $CH_2=C(CH_3)CH_2O(C_2H_4O)_{20}(C_3H_6O)_{29}CH_2C(CH_3)=CH_2$, 43 g of dihydropolydimethyl siloxane $HMe_2SiO(MeSiO)_8—SiMe_2H$, 340 g of toluene, and 20 ppm of platinum as an addition catalyst were reacted. One hundred and eighty-six (186) g of the block copolymer having the following repeated unit and a molecular weight of 90,000 was prepared.

$$[(Me_2SiO)_9Me_2SiCH_2CH(CH_3)CH_2—O(C_2H_4O)_{20}—(C_3H_6O)_{29}CH_2C(CH_3)CH_2]_{26.3}$$

Example 4: Synthesis

Using the same conditions as in Example 1, 120 g of dihydropolydimethyl siloxane $CH_2=C(CH_3)CH_2O(CH_2H_4O)_{18}(C_3H_6O)_{20}CH_2C(CH_3)=CH_2$, 72 g of dihydropolydimethyl siloxane $HMe_2Si(MeSiO)_{15}SiMe_2H$, 330 g of toluene, and 20 ppm of platinum as an addition catalyst were reacted. One hundred and eight-four (184) g of the block copolymer having the following repeated unit and a molecular weight of 71,000 was prepared.

$$[(Me_2SiO)_{16}Me_2SiCH_2CH(CH_3)CH_2—O(C_2H_4O)_{18}(C_3H_6O)_{20}CH_2C(CH_3)CH_2]_{21.5}$$

Example 5: Synthesis

Using the same conditions as in Example 1, 180 g of dimethallyl polyether $CH_2=C(CH_3)CH_2O(C_2H_4O)_5CH_2O(CH_3)=CH_2$, 95 g of dihydropolydimethyl siloxane $HMe_2SiO(MeSiO)_8SiMe_2H$, 350 g of toluene, and 20 ppm of platinum as an addition catalyst. Two hundred and sixty-one (261) g of the block copolymer having the following repeated unit and a molecular weight of 5,000 was prepared obtained.

$$[(Me_2SiO)_9Me_2SiCH_2CH(CH_3)CH_2—O(C_2H_4O)_5CH_2CH(CH_3)CH_2]_{4.8}$$

Example 6; (Control)

Using the same conditions as in Example 1, 27 g of dimethyl polysiloxane containing hydrosilyl groups $Me_3SiO[SiMe_2O]_{100}[SiMeHO]_{13}SiMe_3$, 94 g of allyl polyether $CH_2=CHCH_2O(C_2H_4O)_{18}(C_3H_6O)_{20}CH_3$, 330 g of toluene, and 20 ppm of platinum as an addition catalyst were reacted. One hundred and twenty (120) g of the block copolymer having the following chemical structure and a molecular weight of 35,000 was prepared.

$$Me_3SiO[SiMe_2O]_{100}[SiMeO]_{13}SiMe_3$$
$$|$$
$$C_3H_6O(C_2H_4O)_{18}(C_3H_6O)_{20}CH_3$$

Example 7 (Control)

Using the same conditions as in Example 1, 97 g of dihydropolydimethyl siloxane $HMe_2Si[Me_2SiO]_{200}SiMe_2H$, 43 g of allyl polyether $CH_2=CHCH_2O(C_2H_4O)_{27}(C_3H6O)_{30}CH_3$, 320 g of toluene, and 20 ppm of platinum as an addition catalyst were reacted. One hundred and thirty-three (133) g of the block copolymer having the following chemical structure and a molecular weight of 21,000 was prepared.

$$CH_3(C_2H_4O)_{27}(C_3H_6O)_{30}OC_3H_6(SiO)_{201}—SiMe_2C_3H_6O(C_2H_4O)_{27}(C_3H_6O)_{30}CH_3$$

Example 8: (Hand cream)

A hand cream was prepared by mixing the following ingredients:

| Ingredient | Amount |
|---|---|
| Alternating block copolymer according to Example 1 | 10 weight parts |
| Cyclosiloxane | 24 |
| Squalane | 5 |
| Lanolin | 3 |

-continued

| | |
|---|---|
| Microcrystalline wax | 3 |
| Propyleneglycol | 5 |
| Citric acid | 0.8 |
| Preservative | 0.2 |
| Refined water | 48 |
| Perfume | 1 |
| Polyoxyethylene stearic ester | 3 |

Evaluation:

The hand cream was applied to hands but did not feel sticky. The hands did not feel rough after minutes of dish washing.

Example 9: (Hand Cream Control)

A hand cream was prepared having the same composition as in Example 8 except that the alternating block copolymer was replaced by polyether pendant dimethyl polysiloxane prepared in Example 6.
Evaluation:

Compared with Example 8, the hand cream felt tacky on the hands. After 30 minutes of dish washing, the hand cream was completely removed, and the hands felt coarse and were defatted.

Example 10: (Anti-Sunburn Cream)

An anti-sunburn cream was prepared by mixing the following ingredients:

| | |
|---|---|
| Alternating block copolymer according to Example 2 | 10 weight parts |
| Cyclosiloxane | 40 |
| Squalane | 3 |
| Microcrystalline wax | 1 |
| Silica | 5 |
| Anti-UV agent | 0.5 |
| Citric acid | 0.8 |
| Uroganin acid | 1.0 |
| Preservative | 0.4 |
| Refined water | 30.3 |
| Polyoxyethylene stearic acid | 3 |
| Glycerol | 5 |

Evaluation:

The anti-sunburn cream was applied to a back. The cream exhibited good flow and did not feel tacky sticky. After 10 minutes of swimming in sea water, 50% of the application amount remained.

Example 11: (Lipstick)

A lipstick was prepared by mixing the following ingredients:

| | |
|---|---|
| Alternating block copolymer according to Example 3 | 37 weight parts |
| Microcrystalline wax | 20 |
| Citric acid | 0.5 |
| Titanium oxide fine powder | 8 |
| Siconin | 0.01 |
| Preservative | 0.2 |
| Refined water | 34.29 |

Evaluation:

The lipstick was applied to the skin. The gloss was good. The skin with the lipstick applied to was rinsed with water for 3 minutes, but the purple of Siconin remained.

Example 12: (Lipstick Control)

A lipstick was prepared having the same composition as in Example 11 except that the alternating block copolymer was replaced by polyether pendant dimethylpolysiloxane prepared in Example 6.
Evaluation:

The lipstick was applied to the skin. The gloss was inferior to that of Example 11. After 3 minutes of water rinse shower, the Siconin purple was substantially washed off.

Example 13: (Lotion)

A lotion was prepared by mixing the following ingredients:

| | |
|---|---|
| Alternating block copolymer according to Example 4 | 3 weight parts |
| Stearic acid | 0.2 |
| Cetanol | 1.5 |
| Vaseline | 3.0 |
| Lanolin alcohol | 2.0 |
| Fluid paraffin | 7.0 |
| Polyoxyethylene monooleic acid (10 E.O.) | 2.0 |
| Perfume | 0.5 |
| Preservative | 0.3 |
| Glycerol | 3.0 |
| Propyleneglycol | 5.0 |
| Triethanolamine | 1.0 |
| Refined water | 72.0 |

Evaluation:

The lotion could be very smoothly applied to the skin and prevented smearing of makeup due to sweating. The lotion did not undergo the phase separation.

Example 14: (Lotion Control)

A lotion was prepared having the same composition as in Example 13 except that the alternating block copolymer was replaced by polyether polysiloxane-polyether linear block copolymer prepared in Example 7.
Evaluation:

This lotion was slightly inferior to that according to Example 13 in flow when applied to the skin and allowed smearing of makeup due to sweating.

Example 15: (Cosmetic Liquid)

A cosmetic liquid was prepared by mixing the following ingredients:

| | |
|---|---|
| Alternating block copolymer according to Example 5 | 3.0 weight parts |
| Glycerol | 2.0 |
| Propyleneglycol | 6.0 |
| Dipropyleneglycol | 1.0 |
| Ethanol | 20.0 |
| Refined water | 68.0 |

Evaluation:

This cosmetic liquid had good flow and feel when applied to the skin, made the skin brilliant (glossy) and was felt to tighten the skin.

Example 16: (Cosmetic Liquid Control)

A cosmetic liquid was prepared having the same composition as in Example 15 except that the alternating block copolymer was replaced by polyether pendant dimethyl polysiloxane according to Example 6.

Evaluation:

This cosmetic liquid lacked flow in application to the skin, and gave the skin less brilliance and less tightening feel.

Example 17: (Shampoo)

A shampoo was prepared by mixing the following ingredients:

| | |
|---|---|
| C14-α-olefin natorium sulfonate | 15.0 weight parts |
| Glycerin monostearate | 1.0 |
| Alternating block copolymer according to Example 1 | 1.0 |
| Polyethylene glycol (molecular weight:9,000) distearate | 0.5 |
| Sodium benzoate (germicide) | 1.0 |
| Perfume | 0.5 |
| Yellow No .203 (coloring matter) | 0.01 |
| Citric acid | ph 5.8 |
| Purified water | Balance |

Example 18: (Shampoo Control)

A shampoo was prepared having the same composition as that according to Example 17 except that the alternating block copolymer was replaced by the polyether pendant dimethyl polysiloxane in Example 6.

Evaluation:

Foaming: The shampoo of Example 17 was superior to Example 18 in that the foam felt creamy and was more stable.

Foam extinction: Substantially the same.

Squeaking during rinse: The shampoo of Example 17 squeaked less than Example 18.

Dry condition after hair is dried: The shampoo of Example 17 was less dry.

Example 19: (Hair Spray)

A hair spray was prepared by mixing the following ingredients:

| | |
|---|---|
| Alternating block copolymer according to Example 2 | 12.0 weight parts |
| Ethanol | 16.0 |
| Perfume | 0.5 |
| Trichloromonofluoromethane | 40.0 |
| Dichlorodifluoromethane | 40.0 |

Example 20: (Hair Spray Control)

A hair spray having the same composition as that according to Example 2 was prepared except that the alternating block copolymer was replaced by the polyether pendant dimethyl polysiloxane in Example 6.

Evaluation:

The spray was applied evenly to the hair of a woman (25 cm in length), and the hair was brushed times with a polyethylene brush.

The composition according to Example 19 was superior to the composition according to Example 20 in brilliance, flexibility, smoothness, wetness, brushing, dust attraction and moisture-retention.

Example 21: (Hair Treatment)

A hair treatment was prepared by mixing the following ingredients:

| | |
|---|---|
| Alternating block copolymer according to Example 3 | 10.0 weight parts |
| Lanolin | 1.0 |
| Liquid paraffin | 2.0 |
| Self-emulsifiable glyceride monosterate, | 5.0 |
| Cetyl alcohol | 0.5 |
| Dimethy chloride benzyl-amonium | 3.0 |
| Antiseptics | 0.2 |
| Perfume | 0.1 |
| Purified water | 75.4 |

Example 22: (Hair Treatment Control)

A hair treatment having the same composition as that according to Example 21 was prepared except that the alternating block copolymer was replaced by the polyether-polysiloxane-polyether linear block copolymer in Example 7.

Evaluation:

Example 21 was superior to Example 22 in combing, smoothness, wetness, flexibility, brilliance, voluminousness (bulkiness), moisture-retaining ability and coating effect durability.

Example 23: (Hair Liquid)

A hair liquid was prepared by mixing the following ingredients:

| | |
|---|---|
| Alternating block copolymer according to Example 4 | 5.0 weight parts |
| Polyoxypropylene (30) butyl ether | 10.0 |
| Polyethylene glycol 6000 | 5.0 |
| Ethanol | 44.0 |
| Water | 36.0 |

Example 24: (Hair Liquid Control)

A hair liquid having the same composition as that according to Example 23 was prepared except that the alternating block copolymer was replaced by the polyether pendant dimethyl polysiloxane in Example 6.

Evaluation:

Example 24 is superior to Example 23 in tackiness, combing, wetness, smoothness and voluminousness (bulkiness).

What is claimed is:

1. In a skin cosmetic composition comprising polyether pendant dimethyl polysiloxane and linear polyether-polysiloxane-polyether block copolymers, the improvement which comprises a composition having smooth touch when applied to the skin, non-tackiness, wetness, brilliance, durability on the skin or retention of the beneficial effect the other components and from about 1 to about 37 weight percent of a linear, nonhydrolyzing polysiloxane-polyoxyalkylene block copolymer having the formula:

$$([Y(R_2SiO)_aR_2SiYO][(C_nH_{2n}O)_b])_c$$

wherein R represents a monovalent hydrocarbon radical; n is an integer of 2–4; b is an integer of at least 4; c is an integer of at least 4; a is an integer of at least 5; Y represents a divalent organic group selected from the group consisting of (i) —R"—
(ii) —R"—CO—
(iii) —R"—NHCO—
(iv) —R"—NHCONH—R'"—NHCO— and
(v) —R"—OCONH—R'"—NHCO, wherein R" is an alkylene group selected from the group consisting of ethylene, propylene, butylene, and mixtures thereof and R'" is an arylene group selected from the group consisting of $C_6H_4$—, —$C_6H_4CH_2C_6H_4$—, —$C_6H_4C_6H_4$—, —$C_6H_4CH(CH_3)_2C_6H_4$—, and mixtures thereof; which divalent organic group is bonded with an adjacent silicon atom by a carbon-silicon linkage and with a polyoxyalkylene by an oxygen atom; the average molecular weight of each siloxane block is about 400 to about 10,000; the average molecular weight of each polyoxyalkylene block is about 300 to about 10,000; the siloxane blocks comprise about 10 to about 90 weight percent of the block copolymer; and the block copolymer has an average molecular weight of at least about 3,000.

2. The skin cosmetic composition of claim 1 wherein the skin cosmetic formulation is selected from the group consisting of a cleansing cream, a hand cream, a lotion, and an anti-sunburn cream.

3. A skin cosmetic composition according to claim 1 wherein the block copolymer has an average molecular weight of at least 30,000.

4. A skin cosmetic composition according to claim 1 wherein the block copolymer has the formula:

$$[(Me_2SiO)_{41}Me_2SiCH_2CH(CH_3)CH_2—O(C_2H_4O)_{18}—(C_3H_6O)_{33}CH_2CH(CH_3)CH_2]_{16.1}$$

5. A skin cosmetic composition according to claim 1 wherein the block copolymer has the formula:

$$[(Me_2SiO)_{31}Me_2SiCH_2CH(CH_3)CH_2—O(C_2H_4O)_{20}—(C_3H_6O)_{29}CH_2CH(CH_3)CH_2]_{13.3}$$

6. A skin cosmetic composition according to claim 1 wherein the block copolymer has the formula:

$$[(Me_2SiO)_9Me_2SiCH_2CH(CH_3)CH_2—O(C_2H_4O)_{20}—(C_3H_6O)_{29}CH_2C(CH_3)CH_2]{-}26.3$$

7. A skin cosmetic composition according to claim 1 wherein the block copolymer has the formula:

$$[(Me_2SiO)_{16}Me_2SiCH_2CH(CH_3)CH_2—O(C_2H_4O)_{18}(C_3H_6O)_{20}CH_2C(CH_3)CH_2]_{21.5}$$

8. A skin cosmetic composition according to claim 1 wherein the block copolymer has the formula:

$$[(Me_2SiO)_9Me_2SiCH_2CH(CH_3)CH_2—O(C_2H_4O)_5CH_2CH(CH_3)CH_2]_{4.8}$$

9. A skin cosmetic composition according to claim 1 which is produced by reacting a compound A having the formula:

$$HR_2SiO(R_2SiO)_aSiR_2H$$

with a compound B having the formula:

$$CH_2=\overset{R'}{\underset{|}{C}}CH_2O(C_nH_{2n}O)_bCH_2\overset{R'}{\underset{|}{C}}=CH_2$$

wherein; R represents a monovalent hydrocarbon radical, R' represents a monovalent hydrocarbon radical which may be the same or different from R, n is an integer of 2–4, a is an integer of at least 4 and b is an integer of at least 4.

10. A method for providing smooth touch and durability to skin comprising adding to a skin cosmetic composition about 1 to about 37 weight percent of a linear, non-hydrolyzing polysiloxane-polyoxyalkylene block copolymer having the formula:

$$([Y(R_2SiO)_aR_2SiYO][(C_nH_{2n}O)b])_c$$

wherein R represents a monovalent hydrocarbon radical; n is an integer of 2–4; b is an integer of at least 4; c is an integer of at least 4; a is an integer of at least 5; Y represents a divalent organic group selected from the group consisting of (i) —R"—,
(ii) —R"—CO—,
(iii) —R"—NHCO—,
(iv) —R"—NHCONH—R'"—NHCO— and
(v) —R"—OCONH—R'"—NHCO— wherein R" is an alkylene group selected from the group consisting of —$C_6H_4$—, —$C_6H_4CH_2C_6H_4$—, —$C_6H_4C_6H_4$—, —$C_6H_4CH(CH_3)_2C_6H_4$—, and mixtures thereof and R'" is an arylene group; which divalent organic group is bonded with an adjacent silicon atom by a carbon-silicon linkage and with a polyoxyalkylene block by an oxygen atom; the average molecular weight of each siloxane block is about 400 to about 10,000; the average molecular weight of each polyoxyalkylene block is about 300 to about 10,000; the siloxane blocks comprise about 10 to about 90 weight percent of the block copolymer; and the block copolymer has an average molecular weight of at least about 3,000.

* * * * *